US012667470B2

(12) United States Patent
Ren

(10) Patent No.: US 12,667,470 B2
(45) Date of Patent: Jun. 30, 2026

(54) ANTAGONISTIC DRIVE DEVICE WITH CAPSTANS AND TENDON TRANSMISSION

(71) Applicant: NEUROCEAN TECHNOLOGIES INC., Shenzhen (CN)

(72) Inventor: Hualong Ren, Shenzhen (CN)

(73) Assignee: NEUROCEAN TECHNOLOGIES INC., Shenzhen (CN)

( * ) Notice: Subject to any disclaimer, the term of this patent is extended or adjusted under 35 U.S.C. 154(b) by 1064 days.

(21) Appl. No.: 17/830,972

(22) Filed: Jun. 2, 2022

(65) Prior Publication Data

US 2022/0287852 A1 Sep. 15, 2022

Related U.S. Application Data

(63) Continuation-in-part of application No. PCT/CN2020/133434, filed on Dec. 2, 2020.

(30) Foreign Application Priority Data

Dec. 2, 2019 (CN) .......................... 201911214167.7

(51) Int. Cl.
*A61F 2/58* (2006.01)
*B25J 9/16* (2006.01)
(52) U.S. Cl.
CPC ............. *A61F 2/583* (2013.01); *B25J 9/1633* (2013.01)
(58) Field of Classification Search
CPC .... A61F 2/583; A61F 2/586; A61F 2002/587; B25J 9/1633; B25J 9/1694; B25J 15/0206; B25J 15/0233; B25J 15/024
See application file for complete search history.

(56) References Cited

U.S. PATENT DOCUMENTS

| 8,452,453 B2 | 5/2013 | Zhang et al. |
| 10,188,473 B2 | 1/2019 | Kishi |

(Continued)

FOREIGN PATENT DOCUMENTS

| CN | 102612423 A | 7/2012 |
| CN | 103029135 A | 4/2013 |

(Continued)

OTHER PUBLICATIONS

International Search Report for International Application No. PCT/CN2020/133434; Date of Completion: Feb. 4, 2021; Date of Mailing: Mar. 3, 2021; 5 Pages.

(Continued)

*Primary Examiner* — Adam D Rogers
(74) *Attorney, Agent, or Firm* — CANTOR COLBURN LLP

(57) ABSTRACT

The application discloses an antagonistic drive device which adopts capstans and tendon transmission. The device adopts a pair of rotary actuators which are fixedly connected with the capstans of their respective output shafts respectively to drive the controlled joint and constitute an antagonistic drive. Since the rotary actuator can use a small rotary motor, and the capstans can be arranged properly to make full use of the space in the dexterous hand (especially the forearm) or the robot body. The device has the advantages of small overall size, light weight and low noise, which is especially suitable for driving the joints of dexterous hands with small overall size and a large number of joints. It can also be used for driving the joints of other robots.

11 Claims, 1 Drawing Sheet

(56)                    References Cited

U.S. PATENT DOCUMENTS

Figure 1:
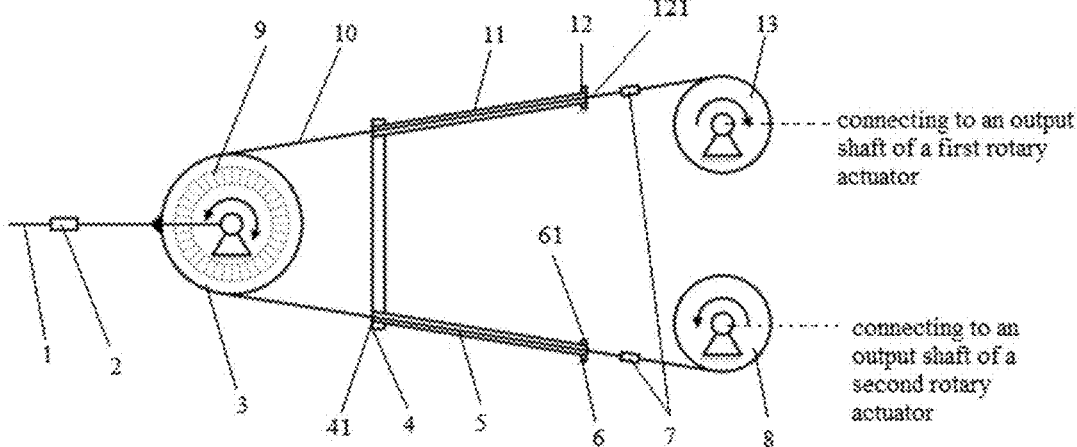

| | | | |
|---|---|---|---|
| 10,321,900 B2 | 6/2019 | Au et al. | |
| 10,342,723 B2 | 7/2019 | Julin | |
| 10,426,636 B2 * | 10/2019 | Mandl | A61F 2/586 |
| 10,661,450 B2 | 5/2020 | Miyazaki et al. | |
| 10,772,740 B2 * | 9/2020 | Poirters | B25J 9/104 |
| 12,251,839 B2 * | 3/2025 | Ren | B25J 9/1633 |
| 2020/0008890 A1 | 1/2020 | Seneci et al. | |
| 2022/0287853 A1 * | 9/2022 | Ren | B25J 13/088 |

FOREIGN PATENT DOCUMENTS

| | | | | |
|---|---|---|---|---|
| CN | 104755041 A | | 7/2015 | |
| CN | 105960311 A | | 9/2016 | |
| CN | 107405250 A | | 11/2017 | |
| CN | 108785010 A | | 11/2018 | |
| CN | 109834725 A | | 6/2019 | |
| CN | 109895079 A | | 6/2019 | |
| CN | 110271020 A | | 9/2019 | |
| CN | 110325139 A | | 10/2019 | |
| CN | 110842968 A | | 2/2020 | |
| CN | 120038769 A | * | 5/2025 | .......... B25J 15/0233 |
| FR | 2560102 A1 | | 8/1985 | |
| GB | 2496335 A | | 5/2013 | |
| WO | 2012049623 A1 | | 4/2012 | |

OTHER PUBLICATIONS

Translation of International Search Report for International Application No. PCT/CN2020/133434; Date of Completion: Feb. 4, 2021; Date of Mailing: Mar. 3, 2021; 3 Pages.

Written Opinion for International Application No. PCT/CN2020/133434; Date of Completion: Feb. 22, 2021; Date of Mailing: Mar. 3, 2021; 4 Pages.

Translation of Written Opinion for International Application No. PCT/CN2020/133434; Date of Completion: Feb. 22, 2021; Date of Mailing: Mar. 3, 2021; 5 Pages.

* cited by examiner connecting to an output
shaft of a first rotary
actuator connecting to an
output shaft of a
second rotary
actuator

ANTAGONISTIC DRIVE DEVICE WITH CAPSTANS AND TENDON TRANSMISSION

CROSS-REFERENCE TO RELATED APPLICATION

This application is a continuation-in-part application of PCT International Application No. PCT/CN2020/133434 filed on Dec. 2, 2020, which claims priority to Chinese patent application No. 201911214167.7 filed on Dec. 2, 2019 and titled "Antagonistic Drive Device with Capstans and Tendon Transmission". The contents each of which are incorporated herein by reference thereto.

TECHNICAL FIELD

This application relates to the driving technology field of bionic dexterous hand, in particular to an antagonistic driving device using capstans and tendon transmission.

BACKGROUND

The bionic dexterous hand refers to a manipulator whose finger amount, degrees of freedom, shape, and function are close to those of a human hand. It can operate objects flexibly and delicately. It is suitable as a high-performance prosthesis or used in flexible assembly and other industrial scenarios, and operations in hazardous environments such as radiation, as well as service robots with high versatility, as it is key components of bionic or humanoid robots. The bionic dexterous hand is characterized by the small hand size and the large number of joints, which requires the transmission of large forces in restricted space, and often requires that each joint can be independently controlled to achieve high flexibility.

At present, most dexterous hands use transmission methods such as tendon transmission, gears or hinged linkage. Among them, tendon transmission has the characteristics of being flexible and capable of transmitting large force to distant joints, and is widely used in dexterous hand systems with a high number of degrees of freedom. This method transfers the force and motion of the actuator located in the arm to the hand joint through the tendon (using steel wire or flexible rope), which can effectively balance the contradiction between the size constraints of the hand space and the need to transmit large forces. In some solutions, a tendon sheath (i.e., a hose) is also put on the outer layer of the tendon, so that the tendon can slide axially within the tendon sheath, which is used to restrain the direction of the tendon and provide protection.

Human joints are driven by a pair of muscle groups in an antagonistic manner, that is, when one group of muscles is tightened and the other group of muscles is released, the corresponding joint is turned in one direction, and vice versa. At present, some dexterous hands that use tendon transmission simulate this method. Each joint is driven by a pair of linear actuators. That is, when the joint needs to be rotated in one direction, one of the actuators pulls the tendon and the other drives the tendon, and vice versa. Linear actuators mainly use pneumatic components (including pneumatic muscles) or hydraulic components, or use rotary motors and lead screw devices to convert the rotary motion of the motor output shaft to linear motion. Solutions for pneumatic components and hydraulic components need to combine a series of supporting components such as pumps, control valves, etc., and the overall volume is large and accompanied by a large noise. For the rotary motor plus the lead screw device scheme, the lead screw weight is large, and the transmission efficiency is low. For these reasons, the above solutions are not suitable for driving finger joints of dexterous hands with a small overall size and a large number of joints.

SUMMARY

One purpose of this application is to provide an antagonistic drive device using capstans and tendon transmission, aiming at solving the problems that the existing dexterous hand joint drive mode cannot simultaneously meet the requirements of small overall size, large number of joints, large transmission force and controllable joint stiffness.

In order to solve the above technical problems, the technical scheme adopted in this application example is as an antagonistic drive device using capstans and tendon transmission, comprising a tendon; a first rotary actuator; a second rotary actuator; a first capstan; a second capstan; a first tendon sheath guide element at joints; a second tendon sheath guide element at the first rotary actuator; a third tendon sheath guide element at the second rotary actuator; a first tendon sheath; a second tendon sheath; and a controlled joint.

The controlled joint comprises a rotational part and a joint base, the rotational part and the joint base are hinged so that the controlled joint can rotate.

The first tendon sheath guide element at joints comprises a first tendon sheath mounting interface through which the tendon can pass.

The first tendon sheath guide element at joints is relatively fixed with the joint base.

The second tendon sheath guide element at the first rotary actuator comprises a second tendon sheath mounting interface through which the tendon can pass.

The second tendon sheath guide element at the first rotary actuator is relatively fixed with the first rotary actuator's stator.

The third tendon sheath guide element at the second rotary actuator comprises a third tendon sheath mounting interface through which the tendon can pass.

The third tendon sheath guide element at the second rotary actuator is relatively fixed with the second rotary actuator's stator.

One end of the first tendon sheath is fixed to the first tendon sheath mounting interface of the first tendon sheath guide element at joints, and the other end of the first tendon sheath is fixed to the second tendon sheath mounting interface of the second tendon sheath guide element at the first rotary actuator.

One end of the second tendon sheath is fixed to the first tendon sheath mounting interface of the first tendon sheath guide element at joints, and the other end of the second tendon sheath is fixed to the third tendon sheath mounting interface of the third tendon sheath guide element at the second rotary actuator.

The rotational part is fixedly connected to any point in the middle of the tendon, the controlled joint is jointly driven by the first rotary actuator and the second rotary actuator, the first rotary actuator is configured to pull one end of the tendon through the first capstan fixed to the first rotary actuator's output shaft, the second rotary actuator is configured to pull the other end of the tendon through the second capstan fixed to the second rotary actuator's output shaft.

The tendon is configured to slide in the first tendon sheath and the second tendon sheath.

The first tendon sheath and the second tendon sheath are hoses. The controlled joint is a dexterous hand's joint, the dexterous hand is a manipulator with at least three fingers and a total of at least six degrees of freedom.

Optionally, the controlled joint is provided with a joint angle sensor.

Optionally, the controlled joint is provided with a joint force and torque sensor.

Optionally, the tendon is provided with one or more tendon tension sensors.

Optionally, the first capstan is provided with a torque sensor to measure torque of the first rotary actuator's output shaft acting on the first capstan.

Optionally, the second capstan is provided with a torque sensor to measure torque of the second rotary actuator's output shaft acting on the second capstan.

Any one of position, velocity, torque, joint damping, and joint stiffness of the controlled joint may be controlled by configuring speed and output forces of the first rotary actuator and the second rotary actuator respectively. Dynamic adjustment of joint damping causes the rotational part of the controlled joint to move in a smooth or burst (such as a flick of the finger) manner. Dynamic adjustment of the joint stiffness of the controlled joint can reduce disturbance by external forces, or flexibly adapt to external forces.

In one embodiment, the first rotary actuator applies a first traction force to the upper part of the tendon, while at the same time the second rotary actuator applies a second traction force to the lower part of the tendon, such that joint damping and/or joint stiffness of the controlled joint are controlled by dynamically adjusting the magnitude of the first traction force and that of the second traction force.

Dynamic adjustment of joint damping causes the rotational end of the controlled joint to move in a smooth or burst (such as a flick of the finger) manner. Dynamic adjustment of the joint stiffness of the controlled joint can make it resist disturbance from external forces, or flexibly adapt to external forces.

In one embodiment, dynamically adjusting the joint damping to cause rotational part of the controlled joint to move in the smooth manner comprises controlling the first traction force applied by the first rotary actuator to the upper part of the tendon and the second traction force applied by the second rotary actuator to the lower part of the tendon, such that the amplitude of the first traction force is close to that of the second traction force.

The amplitude difference between the first traction force and the second traction force may be reduced to make the motion of the controlled joint's rotational end smoother.

In one embodiment, dynamically adjusting the joint damping to cause rotational part of the controlled joint to move in the burst manner comprises controlling the first traction force applied by the first rotary actuator to the upper part of the tendon and the second traction force applied by the second rotary actuator to the lower part of the tendon, so as to increase the amplitude difference between the first traction force and the second traction force.

The amplitude difference between the first traction force and the second traction force may be increased to make the motion of the controlled joint's rotational end closer to an eruption (such as a flick of the finger).

In one embodiment, the amplitude of the first traction force may vary with time and/or load, wherein the amplitude of the second traction force may vary with time and/or load.

The beneficial effects of this application are as follows. The antagonistic drive device with capstans and tendon transmission provided in this application adopts a pair of rotary actuators to drive the controlled joint through the capstans fixedly connected by their respective output shafts, thus constituting an antagonistic drive. The rotary actuator can use a relatively small rotary motor, and the capstans can be arranged properly to make full use of the space in the dexterous hand (especially the forearm). As a result, the device as a whole has small size, light weight, low noise, and is especially suitable for driving finger joints of dexterous hands with small overall size and large number of joints, and can also be used for driving other robot joints.

DRAWINGS OF EMBODIMENTS

In order to more clearly describe the technical solution in this application embodiment, the following is a brief description of the drawings needed for embodiments or demonstration technical descriptions. The following is a brief description of the drawings needed for embodiments or demonstration technical descriptions.

Figure 2:
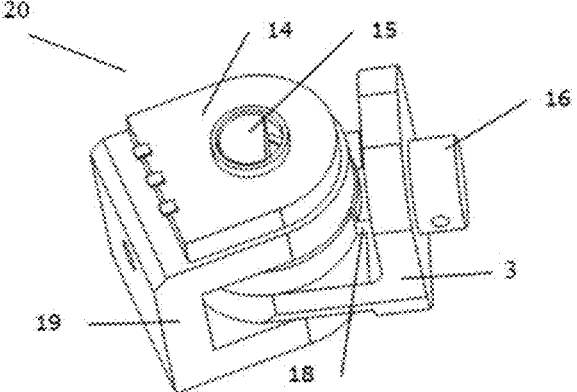

FIG. 1 is a schematic diagram of the overall structure of an antagonistic drive device with capstans and tendon transmission provided in this application example; and FIG. 2 shows a controlled joint diagram of an antagonistic drive device with capstans and tendon transmission provided for this applied embodiment.

DETAILED DESCRIPTION

In order to make the purpose, technical scheme and advantages of this application more clear, the application is explained in detail in combination with the attached drawings and examples. It should be understood that embodiments described herein are intended only to interpret and not to limit this application.

In order to explain the technical scheme of this application, the following details are given in combination with the attached drawings and embodiments.

Referring to FIG. 1, this application proposes an antagonistic drive device using capstans and tendon transmission, comprising: a tendon 10; a first rotary actuator; a second rotary actuator; a first capstan 13; a second capstan 8; a first tendon sheath guide element 4 at joints; a second tendon sheath guide element 12 at the first rotary actuator; a third tendon sheath guide element 6 at the second rotary actuator; a first tendon sheath 11; a second tendon sheath 5; and a controlled joint.

The first rotary actuator and the second rotary actuator are configured with rotary type motors.

The controlled joint comprises a rotational part 3 and a joint base 19 (as shown in FIG. 2), the rotational part and the joint base are hinged so that the controlled joint can rotate.

The first tendon sheath guide element 4 at joints comprises a first tendon sheath mounting interface 41 through which the tendon 10 can pass.

The first tendon sheath guide element 4 at joints is relatively fixed with the joint base.

The second tendon sheath guide element 12 at the first rotary actuator comprises a second tendon sheath mounting interface 121 through which the tendon 10 can pass.

The second tendon sheath guide element 12 at the first rotary actuator is relatively fixed with the first rotary actuator's stator.

The third tendon sheath guide element 6 at the second rotary actuator comprises a third tendon sheath mounting interface 61 through which the tendon can pass.

The third tendon sheath guide element 6 at the second rotary actuator is relatively fixed with the second rotary actuator's stator.

One end of the first tendon sheath 11 is fixed to the first tendon sheath mounting interface of the first tendon sheath guide element 4 at joints, and the other end of the first tendon sheath is fixed to the second tendon sheath mounting interface of the second tendon sheath guide element 12 at the first rotary actuator.

One end of the second tendon sheath 5 is fixed to the first tendon sheath mounting interface of the first tendon sheath guide element 4 at joints, and the other end of the second tendon sheath is fixed to the third tendon sheath mounting interface of the third tendon sheath guide element 6 at the second rotary actuator.

The rotational part 3 is fixedly connected to any point in the middle of the tendon 10, the controlled joint is jointly driven by the first rotary actuator and the second rotary actuator, the first rotary actuator is configured to pull one end of the tendon 10 through the first capstan 13 fixed to the first rotary actuator's output shaft, the second rotary actuator is configured to pull the other end of the tendon 10 through the second capstan 8 fixed to the second rotary actuator's output shaft.

The tendon 10 is configured to slide in the first tendon sheath 11 and the second tendon sheath 5.

The first tendon sheath 11 and the second tendon sheath 5 can be made of rubber tube, PVC, spring tube and other hoses.

The controlled joint is provided with a joint angle sensor 9.

The controlled joint is provided with a joint force and torque sensor 2. In the embodiment of FIG. 1, rotational part 3 is fixedly connected with phalange 1, and joint force and torque sensor 2 is installed at the connection between rotational part 3 and phalange 1.

The tendon is provided with one or more tendon tension sensors 7.

The first capstan 13 is provided with a torque sensor to measure torque of the first rotary actuator's output shaft acting on the first capstan 13.

The second capstan 8 is provided with a torque sensor to measure torque of the second rotary actuator's output shaft acting on the second capstan 8.

Referring to FIG. 2 for an example of an embodiment of this application, the controlled joint is an interphalangeal joint 20, comprising the rotational part 3 of the interphalangeal joint 20 and the interphalangeal joint base 19. Both are hinged through the interphalangeal joint flexion/extension shaft 15. The rotational part 3 of the interphalangeal joint is provided with a V-shaped groove wheel, and the middle point of tendon 10 is fixed to the V-shaped groove wheel of the rotational part 3 of the interphalangeal joint 20 through the tendon fixing element 18, and half wrapped around the V-shaped groove wheel.

The interphalangeal joint angle sensor 14 and the interphalangeal joint force and torque sensor 16 are arranged in the interphalangeal joint.

Referring to FIG. 1, since to judge the motion trend of the controlled joint, one only needs to refer to the motion of the first capstan 13 and second capstan 8. The first rotary actuator and second rotary actuator are hidden in FIG. 1.

Position, velocity, torque, joint damping, and joint stiffness of the controlled joint are controlled by configuring speed and output forces of the first rotary actuator and the second rotary actuator respectively.

1) When the first rotary actuator tightens the upper part of tendon 10 through the first capstan 13, and when the second rotary actuator releases the lower part of tendon 10 through the second capstan 8, the controlled joint rotational part 3 will rotate upward.
2) When the first rotary actuator releases the upper part of tendon 10 through the first capstan 13, and when the second rotary actuator tightens the lower part of tendon 10 through the second capstan 8, the controlled joint rotational part 3 rotates downward.

The joint damping and joint stiffness of the controlled joint can be controlled by dynamically adjusting the traction force on both sides when the first rotary actuator exerts a certain first traction force on the upper part of tendon 10 through the first capstan 13, and the second rotary actuator exerts a certain second traction force on the lower part of tendon 10 through the second capstan 8. The joint damping and/or joint stiffness of the controlled joint can be controlled by dynamically adjusting the amount of traction on both parts. Dynamic adjustment of joint damping causes the rotational end 3 of the controlled joint to move in a smooth or burst (such as a flick of the finger) manner. Dynamic adjustment of the joint stiffness of the controlled joint can make it resist disturbance from external forces, or flexibly adapt to external forces.

Dynamically adjusting the joint damping to cause rotational part of the controlled joint to move in the smooth manner comprises controlling the first traction force applied by the first rotary actuator to the upper part of the tendon and the second traction force applied by the second rotary actuator to the lower part of the tendon, such that the amplitude of the first traction force is close to that of the second traction force.

The amplitude difference between the first traction force and the second traction force may be reduced to make the motion of the controlled joint's rotational end smoother.

Dynamically adjusting the joint damping to cause rotational part of the controlled joint to move in the burst manner comprises controlling the first traction force applied by the first rotary actuator to the upper part of the tendon and the second traction force applied by the second rotary actuator to the lower part of the tendon, so as to increase the amplitude difference between the first traction force and the second traction force.

The amplitude difference between the first traction force and the second traction force may be increased to make the motion of the controlled joint's rotational end closer to an eruption (such as a flick of the finger).

The amplitude of the first traction force may vary with time and/or load, wherein the amplitude of the second traction force may vary with time and/or load.

For example, when the first finger of the dexterous hand has a tendency to perform extension motion but is blocked by the second finger, the second finger constitutes the load, and the corresponding joints of the first finger constitute the controlled joint. By controlling the first rotary actuator and the second rotary actuator, the amplitude of the first traction force and the second traction force of the corresponding tendon are greatly different. When the second finger releases the blocking, the first finger can perform a flick of finger.

The antagonistic drive mechanism based on tendon transmission provides a foundation for the control of joint damping and joint stiffness of dexterous hands, which enables dexterous hands to take into account both the flexibility of operation and the robustness of anti-interference.

The above are only optional embodiments of this application and are not intended to limit this application. This application is subject to various changes and variations for those skilled in the field. Any modification, equivalent replacement, improvement etc. made in the spirit and principle of this application shall be included in the scope of claims of this application.

The invention claimed is:

1. An antagonistic drive device using capstans and tendon transmission, comprising a controlled joint; a tendon; a first rotary actuator; a second rotary actuator; a first capstan; a second capstan; a first tendon sheath guide element at the controlled joint; a second tendon sheath guide element at the first rotary actuator; a third tendon sheath guide element at the second rotary actuator; a first tendon sheath; and a second tendon sheath;

wherein the capstans comprises the first capstan and the second capstan;

wherein the controlled joint comprises a rotational part and a joint base, the rotational part and the joint base are hinged so that the controlled joint can rotate, wherein the first tendon sheath guide element at the controlled joint comprises a first tendon sheath mounting interface through which the tendon can pass, wherein the first tendon sheath guide element at the controlled joint is relatively fixed with the joint base, wherein the second tendon sheath guide element at the first rotary actuator comprises a second tendon sheath mounting interface through which the tendon can pass, wherein the second tendon sheath guide element at the first rotary actuator is relatively fixed with a stator of the first rotary actuator, wherein the third tendon sheath guide element at the second rotary actuator comprises a third tendon sheath mounting interface through which the tendon can pass, wherein the third tendon sheath guide element at the second rotary actuator is relatively fixed with a stator of the second rotary actuator, wherein one end of the first tendon sheath is fixed to the first tendon sheath mounting interface of the first tendon sheath guide element at the controlled joint, and an other end of the first tendon sheath is fixed to the second tendon sheath mounting interface of the second tendon sheath guide element at the first rotary actuator, wherein one end of the second tendon sheath is fixed to the first tendon sheath mounting interface of the first tendon sheath guide element at the controlled joint, and the other end of the second tendon sheath is fixed to the third tendon sheath mounting interface of the third tendon sheath guide element at the second rotary actuator, wherein the rotational part is fixedly connected to any point in the middle of the tendon, wherein the controlled joint is jointly driven by the first rotary actuator and the second rotary actuator, wherein the first rotary actuator is configured to pull one end of the tendon through the first capstan fixed to an output shaft of the first rotary actuator, wherein the second rotary actuator is configured to pull the other end of the tendon through the second capstan fixed to an output shaft of the second rotary actuator, wherein the tendon is configured to slide in the first tendon sheath and the second tendon sheath,

wherein the first tendon sheath and the second tendon sheath are hoses.

2. The antagonistic drive device using capstans and tendon transmission of claim 1, wherein the controlled joint is provided with a joint angle sensor.

3. The antagonistic drive device using capstans and tendon transmission of claim 1, wherein the controlled joint is provided with a joint force and torque sensor.

4. The antagonistic drive device using capstans and tendon transmission of claim 1, wherein the tendon is provided with one or more tendon tension sensors.

5. The antagonistic drive device using capstans and tendon transmission of claim 1, wherein any one of position, velocity, torque, joint damping, and joint stiffness of the controlled joint is controlled by configuring speed and output forces of the first rotary actuator and the second rotary actuator respectively.

6. The antagonistic drive device using capstans and tendon transmission of claim 1, wherein the first rotary actuator is configured to apply a first traction force to an upper part of the tendon, while at the same time the second rotary actuator is configured to apply a second traction force to a lower part of the tendon, controlling joint damping and/or joint stiffness of the controlled joint by dynamically adjusting a magnitude of the first traction force and that of the second traction force.

7. The antagonistic drive device using capstans and tendon transmission of claim 6 being configured to dynamically adjust the joint damping to cause the rotational part of the controlled joint to move in a first manner, and the first manner is a burst manner.

8. The antagonistic drive device using capstans and tendon transmission of claim 7, wherein dynamically adjusting the joint damping to cause the rotational part of the controlled joint to move in the burst manner comprises controlling the first traction force applied by the first rotary actuator to the upper part of the tendon and the second traction force applied by the second rotary actuator to the lower part of the tendon so as to increase an amplitude difference between the first traction force and the second traction force.

9. The antagonistic drive device using capstans and tendon transmission of claim 8, wherein the amplitude difference between the first traction force and the second traction force is configured to be increased so as to make the motion of the rotational end of the controlled joint closer to an eruption.

10. The antagonistic drive device using capstans and tendon transmission of claim 6, being configured to dynamically adjust the joint damping to cause the rotational part of the controlled joint to move in a second manner, the second manner comprises controlling the first traction force applied by the first rotary actuator to the upper part of the tendon and the second traction force applied by the second rotary actuator to the lower part of the tendon so as to reduce an amplitude difference between the first traction force and the second traction force.

11. The antagonistic drive device using capstans and tendon transmission of claim 6, wherein the amplitude of the first traction force is configured to vary with time and/or load, wherein the amplitude of the second traction force is configured to vary with time and/or load.

* * * * *